(12) United States Patent
Lassalle

(10) Patent No.: US 9,945,873 B2
(45) Date of Patent: Apr. 17, 2018

(54) METHODS AND KITS FOR PREDICTING THE RISK OF RESPIRATORY FAILURE, RENAL FAILURE OR THROMBOPENIA IN A SEPTIC PATIENT BY MEASURING ENDOCAN LEVELS IN BLOOD

(75) Inventor: Philippe Lassalle, Lille (FR)

(73) Assignees: INSERM (INSTITUT NATIONAL DE LA SANTE ET DE LA RECHERCHE MEDICALE), Paris (FR); UNIVERSITE DE DROIT ET DE LA SANTE LILLE 2, Lille (FR); CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 729 days.

(21) Appl. No.: 13/980,656

(22) PCT Filed: Jan. 20, 2012

(86) PCT No.: PCT/EP2012/050844
§ 371 (c)(1),
(2), (4) Date: Sep. 16, 2013

(87) PCT Pub. No.: WO2012/098219
PCT Pub. Date: Jul. 26, 2012

(65) Prior Publication Data
US 2014/0017707 A1    Jan. 16, 2014

(30) Foreign Application Priority Data

Jan. 21, 2011 (EP) .................................. 11151656
Oct. 6, 2011 (EP) .................................. 11306293

(51) Int. Cl.
*G01N 33/68* (2006.01)

(52) U.S. Cl.
CPC ..... *G01N 33/6893* (2013.01); *G01N 2800/12* (2013.01); *G01N 2800/222* (2013.01); *G01N 2800/26* (2013.01); *G01N 2800/347* (2013.01); *G01N 2800/50* (2013.01)

(58) Field of Classification Search
None
See application file for complete search history.

(56) References Cited

U.S. PATENT DOCUMENTS 7,473,564 B2 * 1/2009 Lassalle ................. C07K 16/18
435/331

FOREIGN PATENT DOCUMENTS

WO    2010/040538    4/2010

OTHER PUBLICATIONS

Scherpereel et al. "Endocan, a new endothelial marker in human sepsis", Crit Care Med 2006; 34:532-537, DOI: 10.1097/01.CCM.0000198525.82124.74.*
De Freitas et al., "Etude comparative du catabolisme d'endocan humain et murin par les proteases neutrophils humaines et murines," Internet Citation Oct. 12, 2007, p. 34, Retrieved from the Internet: http://www.splf.org/rmr/pdfNR/j2r_2007.pdf [retrieved on Mar. 1, 2009] abstract XP002518044.
De Freitas et al., "Etude de la degradation d'endocan par les neutrophil les et implication dans le sepsis," Internet Citation Dec. 19, 2008, Retrieved from the Internet: http://193.51.50.30/web/7-31.php?ufr=&dadebj=19&dadebm=12&dadeba=2008&dafinj=19&dafinm=12&dafina=2008&lapage=20050156&lang=fr#20050156 [retrieved on Mar. 1, 2009] abstract XP002518046.
International Search Report in PCT/EP2012/050844 dated Jul. 9, 2012, (5 pages total).
Mikkelsen et al., "Lower serum endocan levels are associated with the development of acute lung injury after major trauma," J. Crit. Care, pp. 1-7 (2011) XP007920662.
Pastre et al., "Sepsis 2010," Critical Care, 14(Suppl 2):P42 (2010) XP007920661.

* cited by examiner

*Primary Examiner* — Christine Foster
(74) *Attorney, Agent, or Firm* — Whitham, Curtis & Cook, P.C.

(57) ABSTRACT

The present invention relates to methods and kits for predicting the risk of respiratory failure, renal failure or thrombopenia in a septic patient. More particularly, the present invention relates to a method for predicting the risk of having an organ failure selected from the group consisting of respiratory failure, renal failure and thrombopenia in a septic patient comprising a step consisting of measuring the concentration of endocan in a blood sample obtained from said septic patient.

1 Claim, 4 Drawing Sheets

METHODS AND KITS FOR PREDICTING THE RISK OF RESPIRATORY FAILURE, RENAL FAILURE OR THROMBOPENIA IN A SEPTIC PATIENT BY MEASURING ENDOCAN LEVELS IN BLOOD

The present application is filed pursuant to 35 U.S.C. 371 as a U.S. National Phase application of International Patent Application No. PCT/EP2012/050844, which was filed Jan. 20, 2012, claiming the benefit of priority to European Patent Application No. 11151656.3, which was filed on Jan. 21, 2011 and European Patent Application No. 11306293.9, which was filed on Oct. 6, 2011. The entire text of the aforementioned applications is incorporated herein by reference in its entirety.

FIELD OF THE INVENTION

The present invention relates to methods and kits for predicting the risk of respiratory failure, renal failure or thrombopenia in a septic patient.

BACKGROUND OF THE INVENTION

Sepsis is a clinical syndrome that complicates severe infection and is characterized by systemic inflammation and widespread tissue injury and therefore represents a major cause of admission and mortality in non-coronary intensive care units (ICU). Common causes include gram-negative organisms, staphylococci, and meningococci. There are three recognized stages in the inflammatory response with progressively increased risk of end-organ failure and death: sepsis, severe sepsis, and septic shock. Severe sepsis is sepsis accompanied by signs of failure of at least one organ. Cardiovascular failure is typically manifested by hypotension, respiratory failure by hypoxemia, renal failure by oliguria, and hematologic failure by coagulopathy.

Accordingly methods of predicting the risk of respiratory failure, renal failure or thrombopenia in a septic patient are highly desirable.

Recent results suggest that in septic patients, endocan blood level is related to the severity of illness and the outcome of the patient and may represent a novel endothelial cell dysfunction marker (Scherpereel A, Depontieu F, Grigoriu B, Cavestri B, Tsicopoulos A, Gentina T, Jourdain M, Pugin J, Tonnel A B, Lassalle P. Endocan, a new endothelial marker in human sepsis. Crit Care Med. 2006 February; 34(2):532-7). However the role of endocan for predicting the risk of respiratory failure, renal failure or thrombopenia in a septic patient has not yet been investigated.

SUMMARY OF THE INVENTION

The present invention relates to a method for predicting the risk of having an organ failure selected from the group consisting of respiratory failure, renal failure and thrombopenia in a septic patient comprising a step consisting of measuring the concentration of endocan in a blood sample obtained from said septic patient.

DETAILED DESCRIPTION OF THE INVENTION

The inventors show that blood endocan level represents a tool to predict respiratory failure, and/or renal failure, and/or thrombopenia in septic patients.

Accordingly, the present invention relates to a method for predicting the risk of having an organ failure selected from the group consisting of respiratory failure, renal failure and thrombopenia in a septic patient comprising a step consisting of measuring the concentration of endocan in a blood sample obtained from said septic patient.

As used herein the term "septic patient" refers to a patient having severe sepsis or septic shock.

As used herein the term "respiratory failure" has its general meaning in the art and is defined as the incapacity of the respiratory system to perform its role, that is to say to maintain normal hematose (transformation of venous blood, rich in $CO_2$, to arterial blood, rich in $O_2$). Respiratory failure develops when the rate of gas exchange between the atmosphere and blood is unable to match the body's metabolic demands.

As used herein the term 'renal failure' has its general meaning in the art and describes a medical condition in which the kidneys fail to adequately filter toxins and waste products from the blood.

As used herein the term "thrombopenia" or "thrombocytopenia" has its general meaning tin the art and defines n abnormal decrease in the number of platelets in the blood.

As used herein the term "endocan" or "ESM-1" has its general meaning in the art and refers to the endothelial cell specific molecule-1 that is a 50-kDa dermatan sulfate proteoglycan expressed by endothelial cells in lung and kidney (Lassalle P, Molet S, Janin A, et al: ESM-1 is a novel human endothelial cell-specific molecule expressed in lung and regulated by cytokines. J Biol Chem 1996; 271:20458-20464) and can be detected in human blood (Bechard D, Meignin V, Scherpereel A, et al: Characterization of the secreted form of endothelial-cell-specific molecule 1 by specific monoclonal antibodies. J Vasc Res 2000; 37:417-425; Bechard D, Gentina T, Delehedde M, et al: Endocan is a novel chondroitin sulfate/dermatan sulfate proteoglycan that promotes hepatocyte growth factor/scatter factor mitogenic activity. J Biol Chem 2001; 276:48341-48349).

As used herein the term "blood sample" refers to a whole blood, serum, or plasma sample. Typically the blood sample is prepared at intensive care unit (ICU) admission of the patient with severe sepsis and septic shock.

Once the blood sample from the patient is prepared, the concentration of ESM-1 may be measured by any known method in the art. For example, the concentration of ESM-1 may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, high performance liquid chromatography (HPLC), size exclusion chromatography, solid-phase affinity, etc.

In a particular embodiment, such methods comprise contacting the blood sample with a binding partner capable of selectively interacting with ESM-1 present in the blood sample.

The binding partner may be generally an antibody that may be polyclonal or monoclonal, preferably monoclonal. Polyclonal antibodies directed against ESM-1 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against ESM-1 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g. U.S. Pat. No. 4,946,778) can be adapted to produce anti-ESM-1, single chain antibodies. Antibodies useful in practicing the present invention also include anti-ESM-1 fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to ESM-1. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Anti-ESM-1 monoclonal antibodies are commercially available from Lunginnov (Lille, France). For example, anti-human endocan/ESM-1 antibody MEP08 detects the N-terminus of human endocan (Bechard et al. (2000) J. Vasc. Res. 37:417-425; Grigoriu et al. (2006) Clin. Cancer Res. 12:4575-4582; Maurage et al. (2009) Exp. Neurol. 68:836-844; Leroy et al. (2010) Histopathology 56:180-187; Sarrazin et al. (2010) J. Canc. Sci. Ther. 2:47-52). Anti-human endocan/ESM-1 antibody clone MEP19 detects the C-terminus of human endocan (Bechard et al. (2000) J. Vasc. Res. 37:417-425; Grigoriu et al. (2006) Clin. Cancer Res. 12:4575-4582; Maurage et al. (2009) Exp. Neurol. 68:836-844; Leroy et al. (2010) Histopathology 56:180-187; Sarrazin et al. (2010a) J. Canc. Sci. Ther. 2:47-52; and Sarrazin et al. (2010b) Glycobiology 20:1380-1388).

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as E. coli Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labeling of the probe or antibody by reactivity with a detectable substance. An antibody or aptamer of the invention may be labeled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. Antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against ESM-1. A blood sample containing or suspected of containing ESM-1 is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Typically an ELISA kit is commercially available from Lunginnov (Lille, France): EndoMark H1® (ELISA Kit to detect human endocan). Other ELISA methods are described in: Bechard et al. (2000) J. Vasc. Res. 37:417-425; Grigoriu et al. (2006) Clin. Cancer Res. 12:4575-4582; Leroy et al. (2010) Histopathology 56:180-187; Sarrazin et al. (2006) BBA Reviews 1765:25-37; Sarrazin et al. (2010a) J. Canc. Sci. Ther. 2:47-52; Scherpereel et al. (2003) Cancer Res. 63:6084-6089; Scherpereel et al. (2006) Crit. Care Med. 34(2):532-537.

Measuring the concentration of ESM-1 (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, ESM-1 may be identified based on the known "separation profile" e. g., retention time, for that protein and measured using standard techniques. Alternatively, the separated proteins may be detected and measured by, for example, a mass spectrometer.

The method of the invention is particularly suitable for predicting organ failure, in particular respiratory failure, at 48-72 hours following ICU admission of patients with severe sepsis and septic shock.

The method of the invention further may comprise a step of comparing the concentration of ESM-1 with a predetermined threshold value. Said comparison is indicative whether said patient has a risk to get a respiratory failure, a renal failure or thrombopenia. For example, the predetermined threshold value represents the concentration measured in average in healthy patients, namely patients that will not develop an organ failure. Typically a lower concentration than the predetermined threshold value determined in healthy patients predicts organ failure, more particularly respiratory failure, at 48-72 hours following ICU admission of patients with severe sepsis and septic shock.

The method of the invention may be thus useful for classifying patients affected with sepsis and then may be used to choose the accurate treatment in intensive care unit. For example, patients with a high risk of developing a respiratory failure, a renal failure or thrombopenia may receive a more intensive treatment and attention compared to patient with a weak risk. Such method may thus help the physician to make a choice on a therapeutic treatment which can accordingly consist in administering accurate drugs to the patients. Costs of the treatments may therefore be adapted to the patients admitted in intensive care units, and accordingly the method of the invention may represent a useful tool for the management of such units. Finally, the method of the invention may be applied for monitoring the therapeutic outcome of a patient affected with sepsis.

A further object of the invention relates to the use of ESM-1 as a marker of a respiratory failure, renal failure or thrombopenia in a septic patient.

Yet another object of the invention relates to a kit for predicting the risk of having an organ failure selected from the group consisting of respiratory failure, renal failure or thrombopenia, comprising means for measuring the concentration of ESM-1. The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain means for the detection of other markers of organ failure, such as C reactive protein (CRP) or procalcitonin (PCT), IL-6, TNFa.

The invention will be further illustrated by the following figures and examples. However, these examples and figures should not be interpreted in any way as limiting the scope of the present invention.

BRIEF DESCRIPTION OF THE DRAWINGS

FIG. 2A: levels of endocan in patients without respiratory failure (0), with ALI/ARDS (1) at 48 h (*: p<0.05). FIG. 2B: levels of endocan in patients without respiratory failure (0), with ALI/ARDS (1) at 72 h (*: p<0.05).

FIG. 3A: levels of endocan in patients without respiratory failure (0), with ALI (ALI), with ARDS (SDRA) at 48 h. FIG. 3B: levels of endocan in patients without respiratory failure (0), with ALI (ALI), with ARDS (SDRA) at 72 h.

EXAMPLE 1

Figure 1:
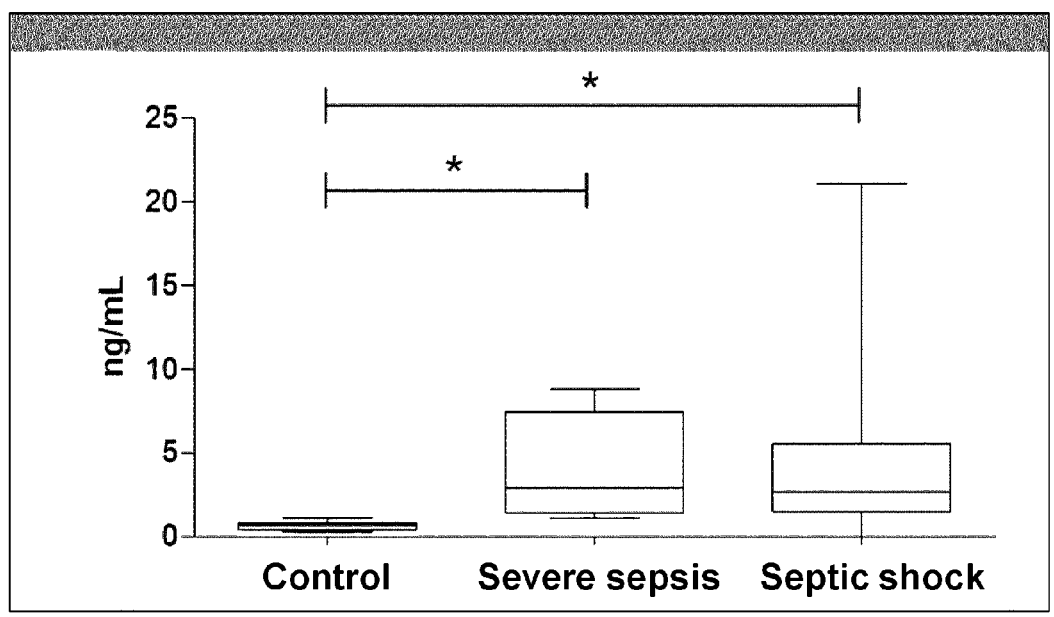
FIG. 1. Increase of endocan plasma levels in severe sepsis (Sepsis Sévère) and septic shock (Choc Septique) patients compared to healthy volunteers (Témoin) (*: p<0.05).

The high level of blood endocan selects septic patients with respiratory failure (defined by $PaO_2/FiO_2<200$), and/or with renal failure (defined by creatinine>20 mg/mL), and/or thrombopenia (Table 1).

TABLE 1

|  | E < 3 ng/mL | E > 3 ng/mL | p |
|---|---|---|---|
| Diuresis after 24 h (mL +/− sem) | 1572 +/− 353 | 1330 +/− 145 | Ns |
| CRP (mg/L +/− sem) | 176 +/− 19.84 | 185 +/− 16.50 | Ns |
| PCT (ng/mL +/− sem) | 17 +/− 4.37 | 46 +/− 17.23 | Ns |
| Platelets (/mm3 +/− sem) | 237600 +/− 27060 | 161400 +/− 16080 | 0.012 |
| Bicarbonate (Bicar) (moy +/− sem) | 24 +/− 0.63 | 22 +/− 0.94 | Ns |
| $PaO_2/FiO_2$ (moy +/− sem) | 237 +/− 21.15 | 168 +/− 15.77 | 0.009 |
| Creatinine (mg/L +/− sem) | 13.5 +/− 1.42 | 20.9 +/− 2.27 | 0.015 |
| Alanine aminotransferase (ALAT) (U/mL +/− sem) | 32 +/− 6.62 | 89 +/− 41.71 | Ns |
| Asparate aminotransferase (ASAT) (U/mL +/− sem) | 60 +/− 16.20 | 124 +/− 33.12 | Ns |
| Total protein (TP) (% +/− SD) | 57 +/− 16 | 53 +/− 22 | Ns |

EXAMPLE 2

Low Levels of Endocan Predicts the Respiratory Failure at 48-72 Hours Following ICU Admission in Patients with Severe Sepsis and Septic Shock Introduction:

Acute lung injury (ALI) and acute respiratory distress syndrome (ARDS) are common clinical disorders characterized by alveolar epithelial and endothelial injury leading to the development of an acute respiratory failure. They are distinguished by pulmonary gas exchange. The term ALI refers to patients with a $PaO_2/FiO_2$ ratio of <300 mmHg, whereas a ratio of <200 mmHg defines ARDS. Both ALI and ARDS may occur either as a direct pulmonary injury, such as pneumonia, aspiration, pulmonary contusion, or toxic inhalation, or an indirect extrapulmonary insult such as sepsis, which is the most prevalent and lethal cause of ARDS, but also multiple transfusions of blood products, acute pancreatitis, non-thoracic trauma with shock, disseminated intravascular coagulation (DIC). The incidence of ALI or ARDS was estimated 7.1% of all patients admitted to an intensive care unit (ICU). The mortality rate associated with ARDS and ALI was estimated 30-40%. For most ARDS patients, the clinical outcome is determined in the first 7-10 days after diagnosis, since within this period, half of the patients have died or have been weaned off mechanical ventilation. Survivors of ARDS recover lung function over 6-12 months but residual abnormalities, including mild restriction/obstruction, impaired gas exchange during exercise, or lowered diffusion capacity, often remain.

Prognostic indicators for increased mortality include advanced age, the presence of non-pulmonary organ dysfunction, liver cirrhosis, active malignancy, and septic shock; whereas the initial degree of gas exchange impairment is a poor predictor of the clinical outcome. A simple, accurate and blood-based biomarker able to assess the initial severity ALI/ARDS and to closely follow the evolution of the inflammatory phenomenon would be hugely helpful for clinicians to predict outcome and to more appropriately select therapeutic measures.

ALI/ARDS can be divided into exudative, proliferative and fibrotic phases with significant overlaps. The exudative phase occurs in the acute early phase (1-7 days after injury) and is characterized by diffuse alveolar damage (DAD) with necrosis of alveolar type I cells, interstitial and alveolar protein-rich edema, hemorrhage, and diffuse neutrophilic alveolar infiltrates. The proliferative phase starts typically 1-2 weeks after the original insult and is characterized by proliferation and hyperplasia of alveolar type II cells, and by proliferation of fibroblasts in the interstitium and later within the alveolar lumen. Only some patients enter the fibrotic phase, typically starting 10-14 days after initial injury. It is characterized by accumulation of lymphocytes and macrophages, as well as fibrosis, and tortuous vessels narrowed by myointimal thickening and mural fibrosis.

Neutrophils are regarded as the main players in inflammatory processes associated with ALI/ARDS. They accumulate in both lung tissue and bronchoalveolar lavage fluid from patients with ARDS. Neutrophils fight invading microorganisms but can also cause cell damage by the production and secretion of proinflammatory mediators, free radicals, reactive oxygen species, and proteases. These findings support the notion that neutrophil-dependant inflammation is not only the result but also the cause of ALI. However, specific regulatory mechanisms that control accumulation of PMN in the lung during ALI/ARDS are not completely understood.

The main target damage in case of indirect injury such as that observed in sepsis is the pulmonary endothelium. Our understanding of the mechanisms that govern the pathophysiological responses of endothelial cells in ARDS remains incomplete. Endothelial injury increases vascular permeability and thus promotes the formation of pulmonary edema. However, endothelial cells may also be activated independently of any cellular damage, including (i) induction of local coagulation resulting in excessive fibrin deposition, (ii) overexpression of adhesion molecules such as ICAM-1, favoring leukocyte recruitment and migration into the interstitium and the alveolar spaces. This can relate to an increase of soluble ICAM-1 in severe sepsis, however, ICAM-1 is also expressed on fibroblasts and leukocytes, reducing the selectivity of sICAM-1 expression to pulmonary endothelium. In addition, capillary pulmonary endothelium is characterized by the absence of expression of 2 other major adhesion molecules E-selectin and VCAM-1, even upon activated capillary endothelium from lung ARDS.

In another hand, there are emerging and consistent data that can consider endocan as a biomarker of activated-pulmonary vascular endothelial cells. Endocan (or ESM-1) has been identified as an endothelial cell specific proteoglycan constituted of a protein core of 20 kDa and a unique glycosaminoglycan chain of chondroitin sulphate/dermatan sulphate, O-linked to the serine 137. Endocan is mainly expressed by lung, and in a lesser extent, by kidney capillaries. Lung capillary selectivity is driven by a short promoter sequence Cytokines like TNF or IL-1 or bacterial LPS trigger the synthesis and secretion of endocan by endothelial cells. Endocan binds to its receptor the leukocyte integrin LFA-1 and inhibits the LFA-1/ICAM-1 interaction, suggesting a role for endocan in the control of leukocyte diapedesis. Early studies have demonstrated that blood levels of endocan are increased in patients with severe sepsis, performing as a bad prognosis signature as well as procalcitonin, presently the best prognosis marker of sepsis.

To explain how ALI/ARDS can occur during sepsis, we hypothesize that soon after pulmonary bacterial challenge, activated macrophages release IL-8 in order to recruit neutrophils, and TNFα which in turn activates lung endothelial cells to express ICAM-1 and endocan in order to control leukocyte diapedesis. But if the sepsis is severe enough to induce intravascular neutrophil activation, endocan proteolysis induced by neutrophil proteases occurs, leading to exacerbate neutrophil diapedesis and to trigger organ failure. If our hypothesis is true, we then should be able to find a link between the kinetics of endocan, and occurrence of respiratory failure during severe sepsis.

Patients and Methods:

Twenty one patients and nine normal volunteers have been prospectively enrolled in the present study. All patients came from the Intensive Care Unit at Lille University Hospital. The inclusion criteria were patients with severe sepsis or septic shock, according to the ACC/SCCM classification. The non inclusion criteria were age<18 years old and pregnancy. The exclusion criteria were septic shock with non septic origin, and immunosuppressive therapies 1 month before the admission in ICU.

Indices of organ dysfunction were collected at the inclusion and at 24 h, 48 h and 72 h: Glasgow coma scale≤14, $PaO_2 \leq 9.75$ kPa, oxygen saturation≤92%, ALI ($PaO_2/FiO_2 \leq 300$), ARDS ($PaO_2/FiO_2 \leq 200$), systolic blood pressure≤90 mmHg, systolic blood pressure fall≥40 mmHg from baseline, pH≤7.3, lactate≥2.5 mmol/l, creatinine≥177 μmol/l, doubling of creatinine in patients with known kidney disease, oliguria≤30 ml/hour for >3 hours or ≤0.71/24 hours, prothrombin time≤0.6 s (reference 0.70-1.30 s), platelets≤100×109/l, bilirubin≥43 μmol/l, and paralytic ileus. Septic shock was defined as hypotension persisting despite adequate fluid resuscitation for at least 1 hour.

Blood were sampled in 5 mL citrate tube from the included patients at ICU admission. The samples are then centrifuged at 3000 g for 15 min at 4° C., aliquoted by 500 μL plasma per tube, and then frozen at −80° C. within 1.5 hours. The endocan levels were determined by ELISA (Lunginnov, France).

Data were presented as the median and interquartile range or as the mean±standard deviation. Data analysis included comparison by variance analysis of endocan plasma levels at the inclusion and the presence or absence of each organ failure at each time point of the study. When significant, groups were compared 2 by 2 using post-hoc tests with Bonferroni correction. The prognostic value of endocan was done by ROC curve. All statistical calculations will be performed with the SPSS statistical software package.

Results:

Endocan plasma levels were increased in severe sepsis (3.96±3.35 ng/mL) and in septic shock (4.33±5.01 ng/mL) versus healthy controls (0.67±0.25 ng/mL) (p<0.05) (FIG. 1).

Figures 2A, 2B:
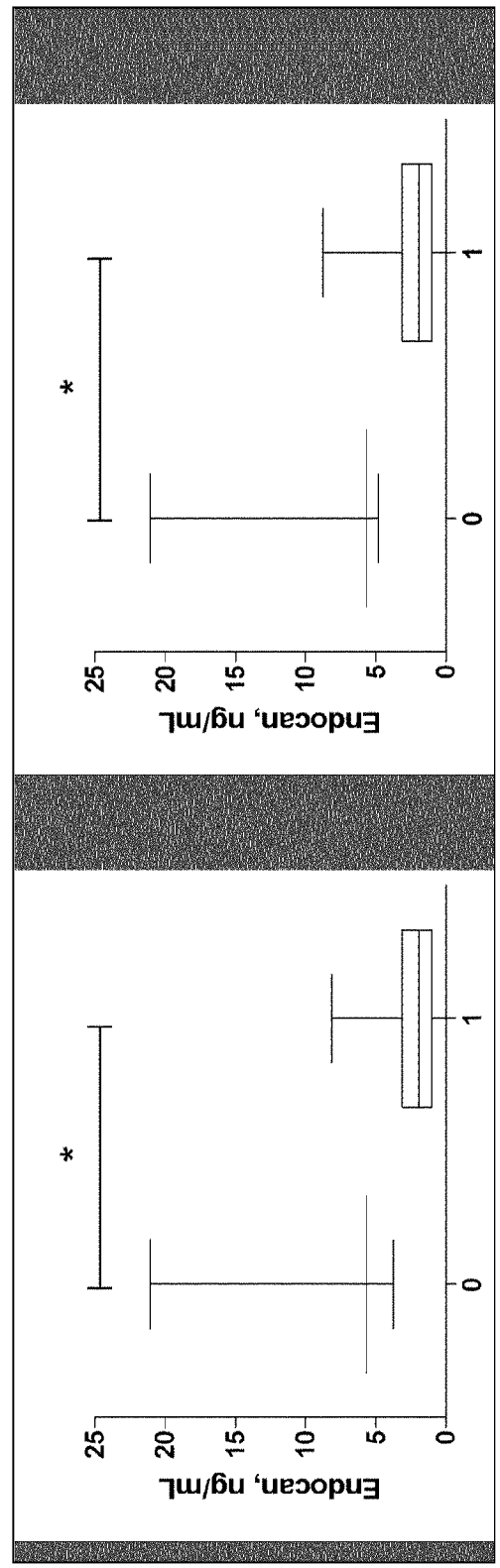
FIG. 2A-2B. Endocan and respiratory failure.

Patients with respiratory failure at 48 h and/or 72 h revealed significant low levels of plasma endocan at the inclusion than patients without respiratory failure at the same time points (p<0.05, FIG. 2).

Figure 3A:
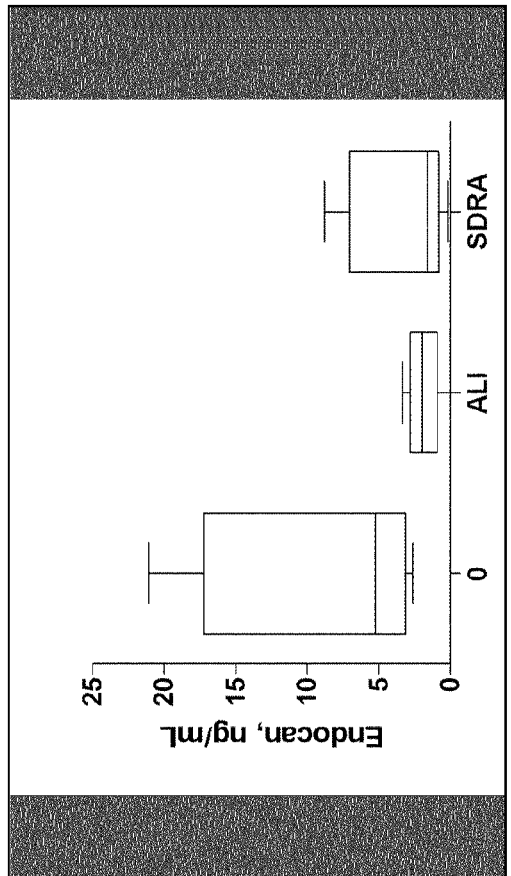
FIG. 3A-3B. Endocan and respiratory severity.
Figure 3B:
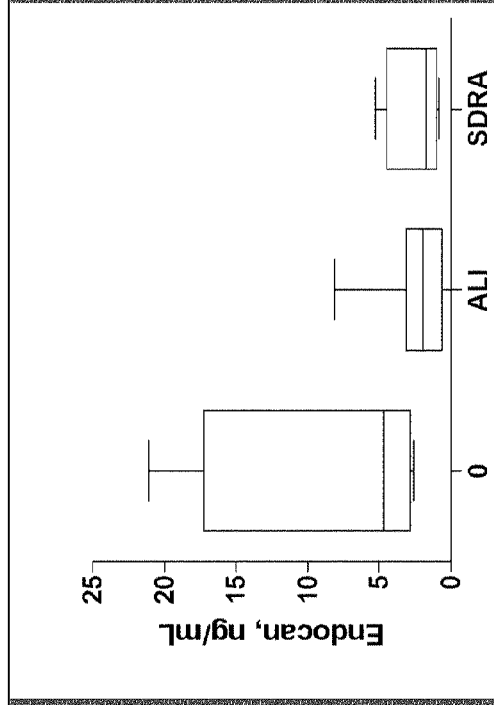

The plasma levels of endocan did not discriminate ALI from ARDS. They were low in both groups (FIG. 3).

Figure 4:
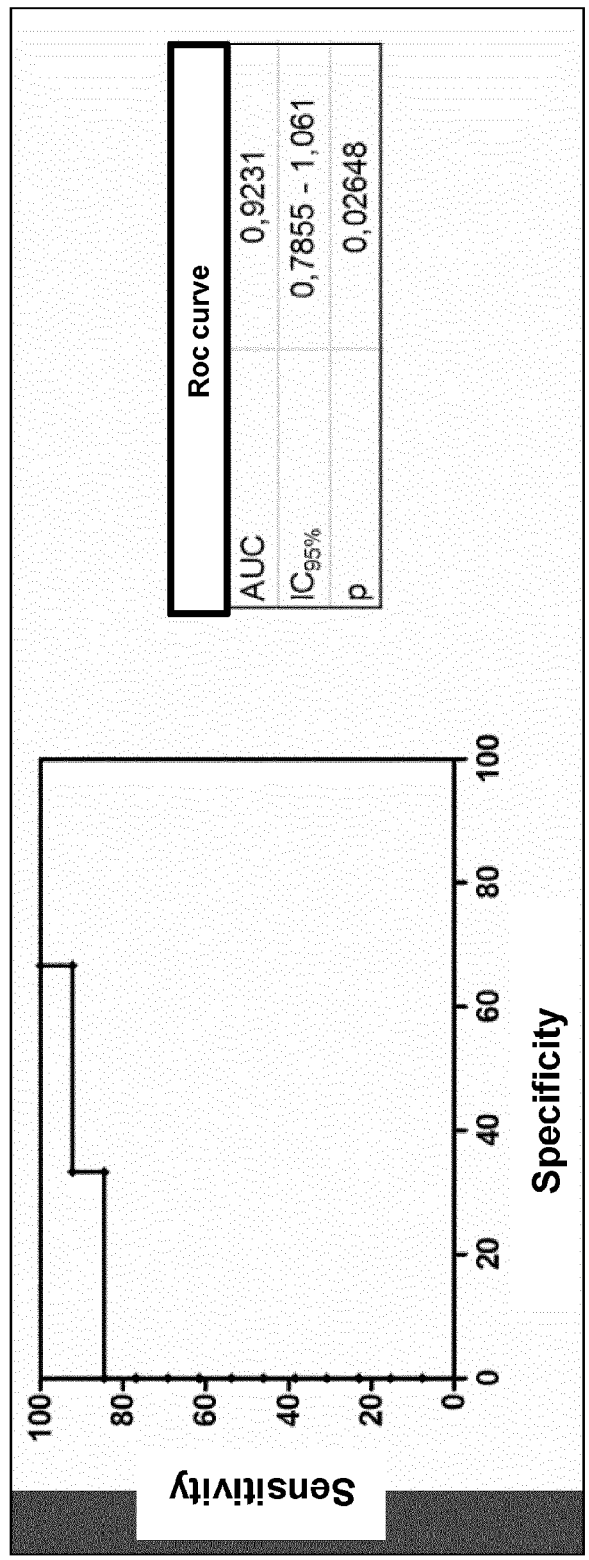
FIG. 4. ROC curve of endocan plasma levels at the inclusion with the presence of respiratory failure at 48 h. AUC: Area Under the Curve. The table under the graph indicates the calculated sensitivity and specificity depending on the value of endocan plasma levels. The grey cases establish the endocan cut off (3.55 ng/mL) for best sensitivity/specificity value (84.62%, 100%, respectively).

The ROC curve between endocan and the respiratory failure at 48 h indicated an AUC=0.923 (p<0.05). Values of endocan<3.55 ng/mL at the admission predicts the respiratory failure at 48 h with 84.62% sensitivity and 100% specificity (FIG. 4).

REFERENCES

Throughout this application, various references describe the state of the art to which this invention pertains. The disclosures of these references are hereby incorporated by reference into the present disclosure.

The invention claimed is:

1. A method for predicting the risk of developing respiratory failure in a septic patient and treating said septic patient comprising the steps of:
    measuring the concentration of endocan in a blood sample obtained from said septic patient,
    comparing the concentration of endocan with a predetermined threshold value representing the concentration measured in average in patients that will not develop respiratory failure,
    determining that said septic patient is at risk for respiratory failure at 48-72 hours following ICU admission when the concentration of endocan is lower than the predetermined threshold value, and
    treating said septic patient determined to be at risk for respiratory failure by administering a therapy for respiratory failure, wherein said therapy for respiratory failure includes mechanical ventilation.

* * * * *